(12) United States Patent
Berelsman et al.

(10) Patent No.: US 9,572,563 B2
(45) Date of Patent: Feb. 21, 2017

(54) SUTURE ANCHOR AND RELATED METHOD

(71) Applicant: Biomet Sports Medicine, LLC, Warsaw, IN (US)

(72) Inventors: Brian K. Berelsman, Warsaw, IN (US); Kevin T. Stone, Winona Lake, IN (US)

(73) Assignee: Biomet Sports Medicine, LLC., Warsaw, IN (US)

( * ) Notice: Subject to any disclaimer, the term of this patent is extended or adjusted under 35 U.S.C. 154(b) by 446 days.

(21) Appl. No.: 14/022,378

(22) Filed: Sep. 10, 2013

(65) Prior Publication Data

US 2015/0012015 A1    Jan. 8, 2015

Related U.S. Application Data

(60) Provisional application No. 61/843,660, filed on Jul. 8, 2013.

(51) Int. Cl.
*A61B 17/04* (2006.01)

(52) U.S. Cl.
CPC .... *A61B 17/0401* (2013.01); *A61B 2017/0409* (2013.01); *A61B 2017/0412* (2013.01); *A61B 2017/0414* (2013.01); *A61B 2017/0445* (2013.01)

(58) Field of Classification Search
CPC ................. A61B 17/0401; A61B 2017/0409; A61B 2017/0464; A61B 2017/0414; A61B 2017/0496; A61B 2017/0445; A61F 2002/0882; B25B 31/00
See application file for complete search history.

(56) References Cited

U.S. PATENT DOCUMENTS

| | | | |
|---|---|---|---|
| 5,718,717 A * | 2/1998 | Bonutti | A61B 17/0401 606/139 |
| 6,685,728 B2 | 2/2004 | Sinnott et al. | |
| 6,840,953 B2 | 1/2005 | Martinek | |
| 7,331,982 B1 | 2/2008 | Kaiser et al. | |
| 7,780,701 B1 | 8/2010 | Meridew et al. | |
| 8,435,264 B2 | 5/2013 | Sojka et al. | |
| 8,460,340 B2 | 6/2013 | Sojka et al. | |
| 8,623,052 B2 | 1/2014 | Dreyfuss et al. | |
| 2010/0198258 A1* | 8/2010 | Heaven | A61B 17/0401 606/232 |
| 2010/0222812 A1 | 9/2010 | Stone et al. | |
| 2013/0345747 A1 | 12/2013 | Dreyfuss | |

* cited by examiner

*Primary Examiner* — Katherine M Shi
*Assistant Examiner* — Michael Mendoza
(74) *Attorney, Agent, or Firm* — Schwegman Lundberg & Woessner, P.A.

(57) ABSTRACT

A method and apparatus for securing soft tissue to bone can include loading a suture through an eyelet of a suture anchor. The suture anchor can have a longitudinal axis and a distal tip. An anchor inserter assembly can be positioned in contact with the suture anchor. The anchor inserter assembly can include a sleeve portion and an impacting portion. The suture can be engaged with a suture engaging member on the suture inserter assembly at a location adjacent to the eyelet. The sleeve portion can be translated relative to the impacting portion from an alignment position to an insertion position thereby moving the suture a first distance offset from the eyelet in a direction away from the distal tip. The anchor insert assembly can be advanced to a driven position thereby advancing the suture anchor into the bone. The suture engaging member can be released from the suture.

10 Claims, 8 Drawing Sheets

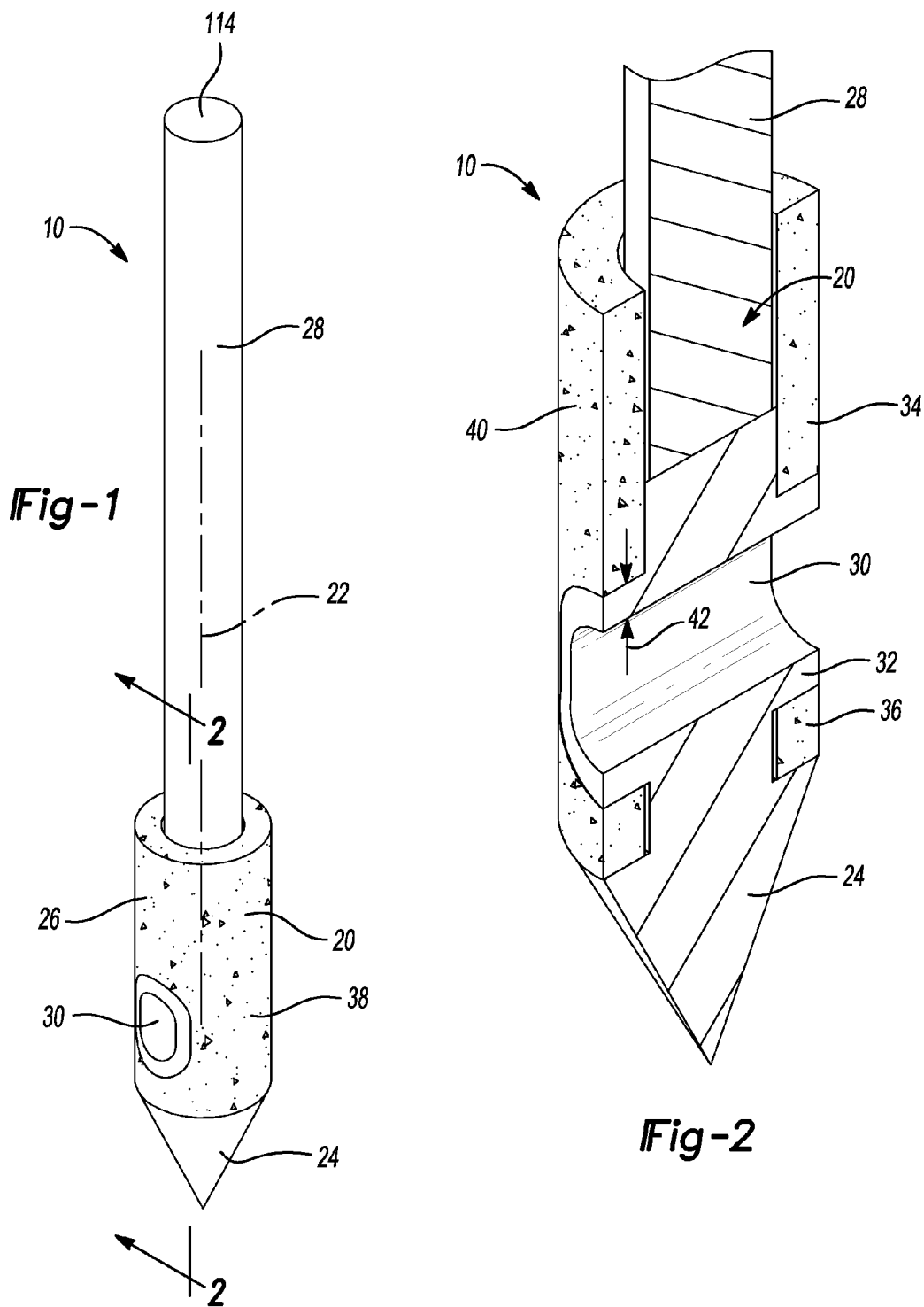

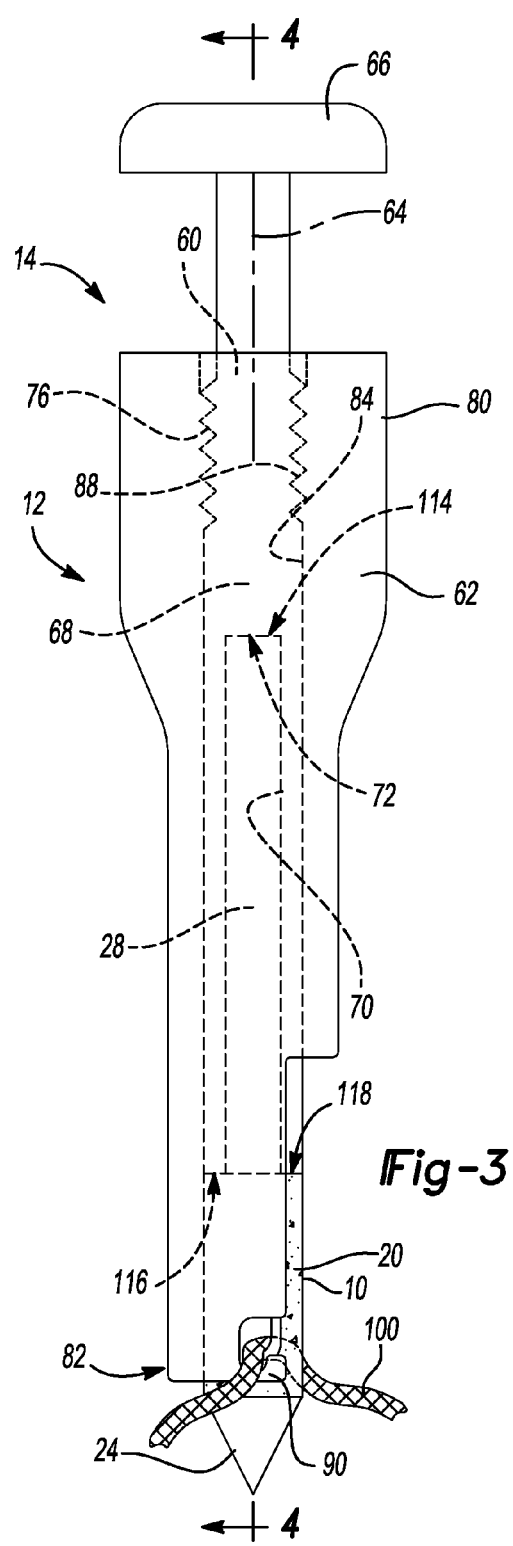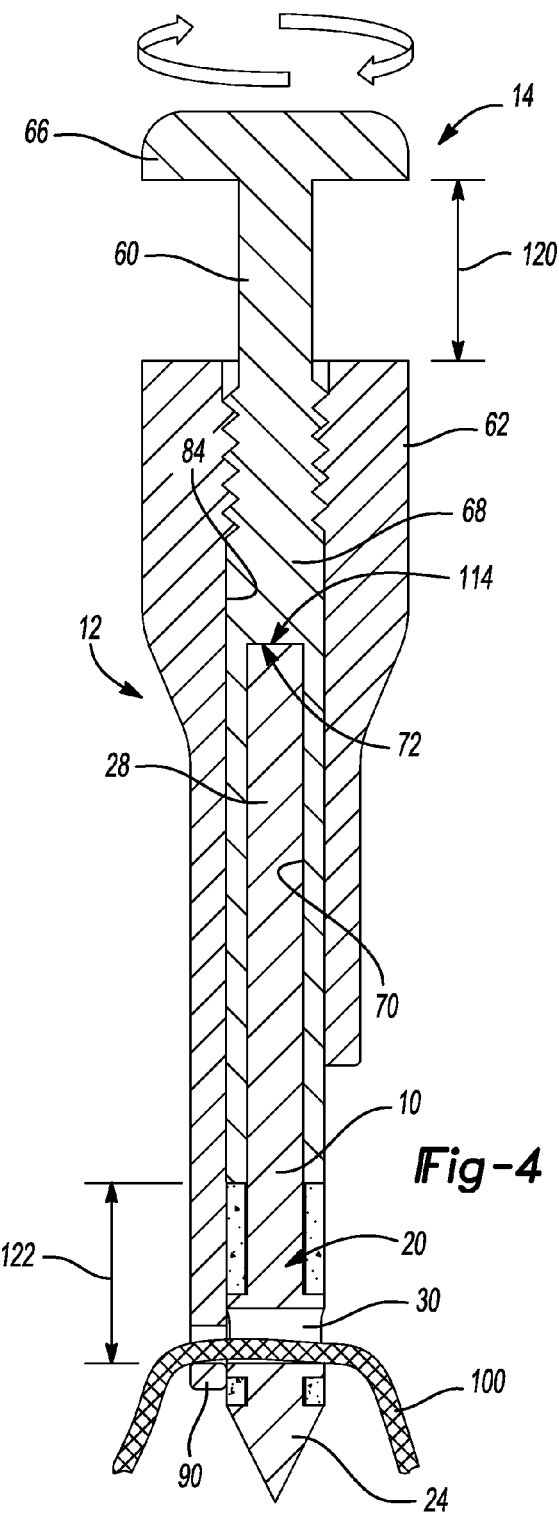
Fig-3
Fig-4

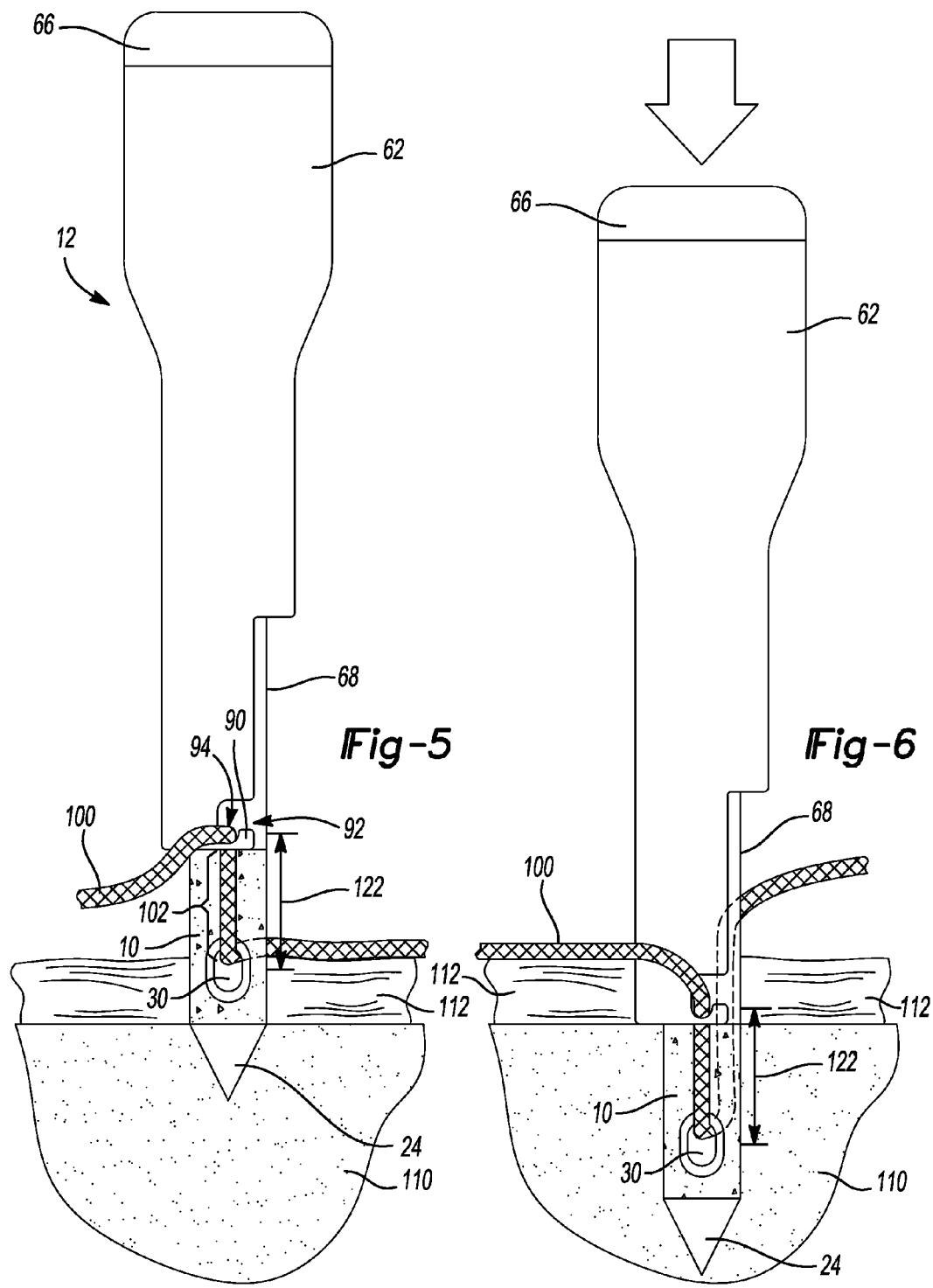

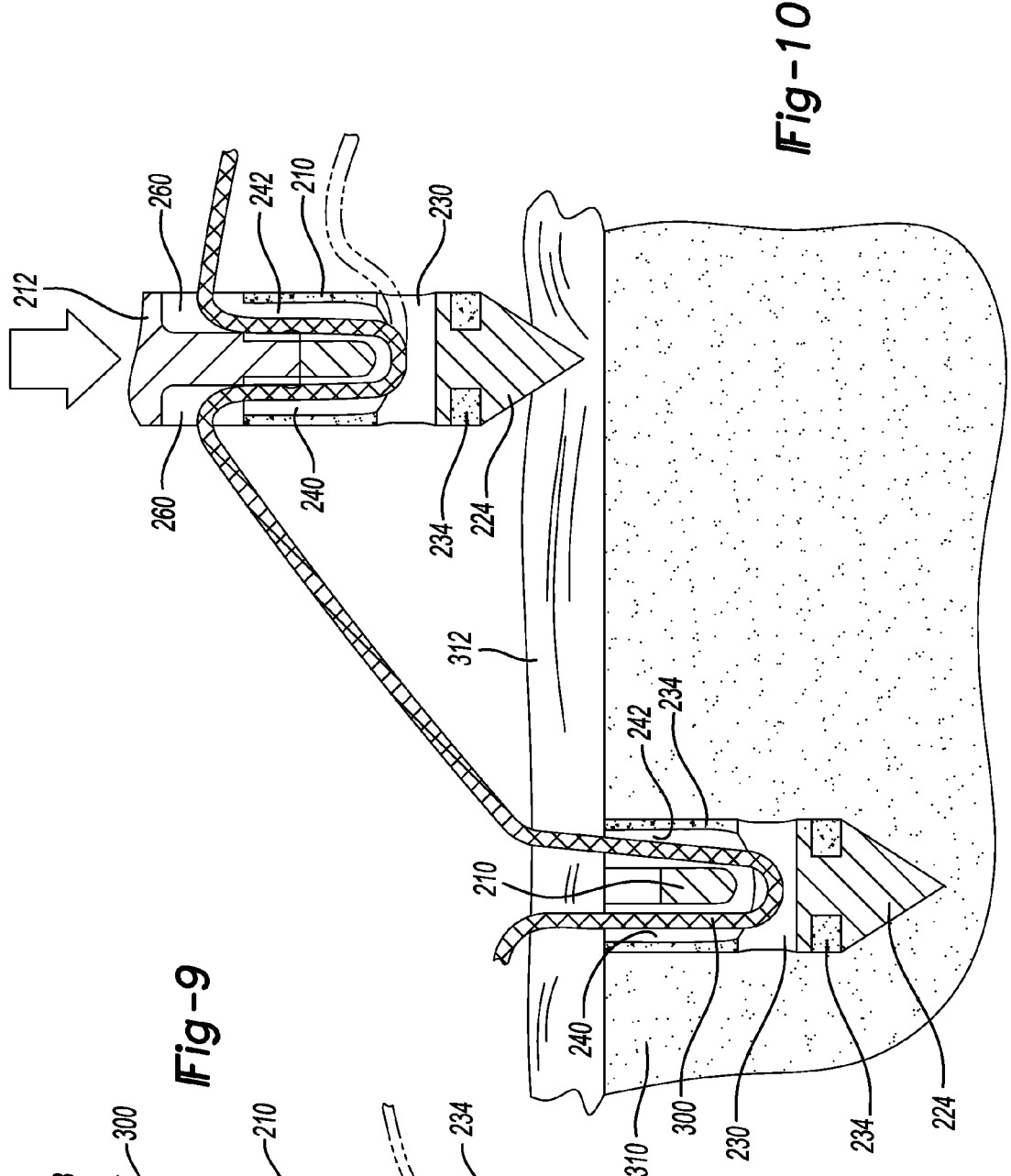

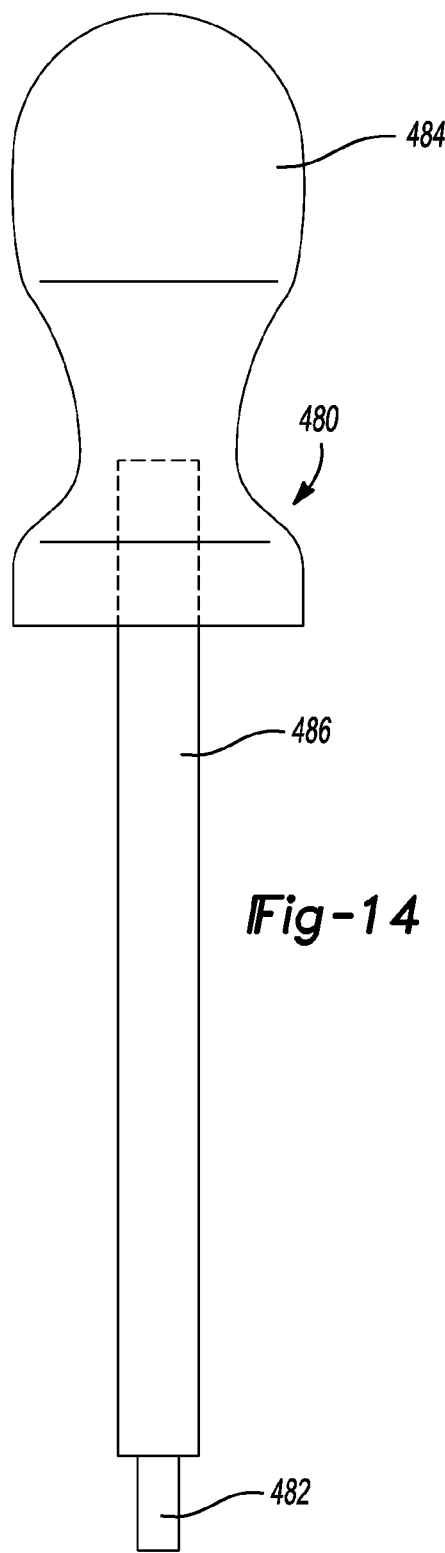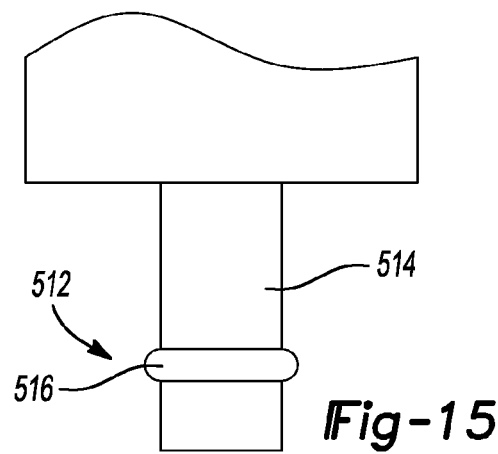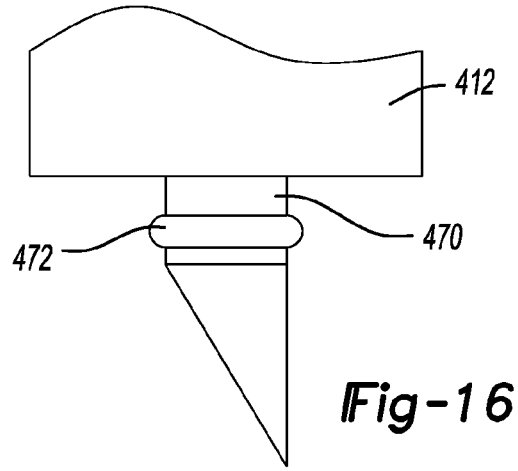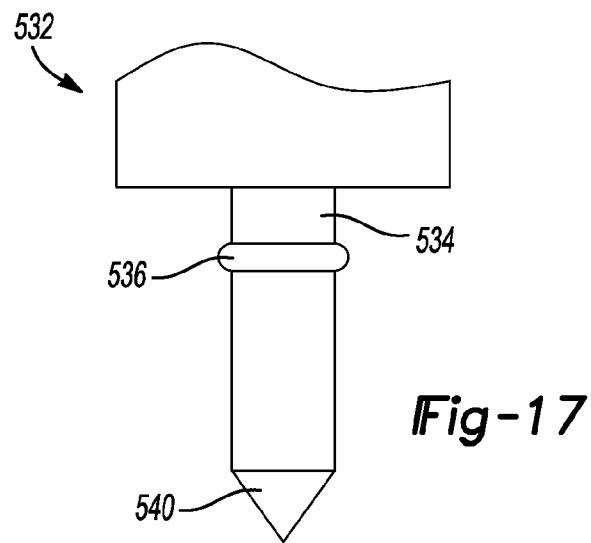

SUTURE ANCHOR AND RELATED METHOD

RELATED APPLICATIONS

This application claims the benefit of priority from U.S. Provisional Application No. 61/843,660, filed Jul. 8, 2013, which is incorporated by reference herein in its entirety.

FIELD

The present disclosure relates generally to an apparatus and method for use in orthopedic surgical procedures. More particularly, the present disclosure relates to a suture anchor system and method for securing soft tissue, tendons and ligaments to bone during orthopedic surgical procedures.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair or replace various portions thereof. For example, the soft tissues of the body may need to be reattached to bones due to trauma, overuse, surgical intervention, or disease. Soft tissue can be reattached to bone using devices such as screws, staples, and various types of suture anchors. One means to fix the soft tissue to the selected area is to provide a suture through a selected portion of the soft tissue and fix the other end of the suture to a selected area on the bone using a suture anchor and a pre-formed hole in the bone, which can require various different instruments and tying a knot to secure the suture to the anchor. Accordingly, there is a need for improvement in the relevant art.

SUMMARY

This section provides a general summary of the disclosure, and is not a comprehensive disclosure of its full scope or all of its features.

A method for securing soft tissue to bone can include loading a suture through an eyelet of a suture anchor. The suture anchor can have a longitudinal axis and a distal tip. An anchor inserter assembly can be positioned in contact with the suture anchor. The anchor inserter assembly can include a sleeve portion and an impacting portion. The suture can be engaged with a suture engaging member on the suture inserter assembly at a location adjacent to the eyelet. The sleeve portion can be translated relative to the impacting portion from an alignment position to an insertion position thereby moving the suture a first distance offset from the eyelet in a direction away from the distal tip. The anchor insert assembly can be advanced to a driven position thereby advancing the suture anchor into the bone. The suture engaging member can be released from the suture.

According to additional features, a desired amount of tension can be applied on the suture subsequent to translating the sleeve portion. The suture anchor can be advanced into the bone a second distance. The first and second distances can be substantially equivalent such that the desired amount of tension on the suture is substantially constant from the insertion position to the driven position. In one example, the sleeve portion can be threadably advanced relative to the impacting portion. Translating the sleeve portion can cause the suture engaging member to slidably engage the suture while the suture engaging member moves from the alignment position to the insertion position. In the alignment position, a hook of the suture engagement member is aligned with the eyelet.

In other features, releasing the suture engaging member can include rotating the sleeve relative to the impacting portion around a longitudinal axis of the anchor inserter assembly. Engaging the suture with the suture engaging member can include engaging a first portion of the suture extending out of one side of the eyelet with the suture engaging member. A desired amount of tension on the suture can be confirmed on a portion of the suture extending out of an opposite side of the eyelet. Advancing the suture anchor into the bone can include impacting an impacting plate on the impacting portion. The impacting can cause an impacting force to be transferred from the impacting portion to the suture anchor. Positioning the anchor inserter assembly can include advancing a proximal stem of the suture anchor into a blind bore of the impacting portion. A terminal proximal end of the proximal stem can be contacted with an engaging surface of the blind bore.

A suture securing assembly for use in securing a suture relative to bone can include an impacting portion, a sleeve portion and an anchor. The impacting portion can extend along a first longitudinal axis. The impacting portion can have a strike plate and a shaft portion that defines a suture anchor engaging surface. The sleeve portion can be movably coupled to the impacting portion. The sleeve portion can have a central passage that receives the impacting portion therethrough. The sleeve portion can have a suture engaging member formed at a distal end. The anchor can have an anchor body that includes a distal tip portion and an impactor engaging surface. The anchor body can define an eyelet. The proximal stem portion can be configured to be slidably received by the suture anchor engaging surface. The sleeve portion can be configured to translate relative to the impacting portion along the first longitudinal axis from an alignment position where the suture engaging member is aligned with the eyelet to an insertion position where the suture engaging member moves the suture to a location offset a distance from the eyelet in a direction away from the distal tip.

According to additional features, the sleeve portion can be threadably coupled to the impacting portion. Rotation of the sleeve portion about the first longitudinal axis can cause the sleeve portion to translate relative to the impacting portion. The suture engaging member can comprise a hook. The strike plate can be configured to engage the sleeve portion at the insertion position thereby inhibiting further relative translation of the sleeve portion and the impacting portion. The anchor body can include a solid anchor portion and a porous anchor portion. The eyelet can be defined by the solid anchor portion.

A suture anchor for securing a suture relative to bone can include an anchor body that extends along a longitudinal anchor body axis. The anchor body can include a distal tip portion and a proximal body portion. The anchor body can define an eyelet. The anchor body can further comprise a solid anchor portion and a porous anchor portion wherein the eyelet is defined by the solid anchor portion.

According to additional features, the anchor body can further comprise a first and a second longitudinal opening extending from a proximal terminal end surface of the anchor body to the eyelet. The first and second longitudinal openings can be defined by the solid anchor portion. The first and second longitudinal openings can be parallel to the longitudinal anchor body axis. In one example, the anchor body can include at least one flexible wing portion extending outwardly from the anchor body. The flexible wing portion can be configured to contract during insertion into bone and provide a radially outwardly biasing force onto surrounding bone subsequent to insertion.

According to still other features, the eyelet can be formed through the anchor body from a first opening at the proximal terminal end surface of the anchor body to a second opening through an outer cylindrical wall of the anchor body. First and second flexible wings can be formed on diametrically opposed portions the suture anchor. The first opening can be defined through the first flexible wing.

According to yet other features, an insertion tool can selectively and removably couple with the suture anchor for driving the suture anchor into bone. The insertion tool can comprise a distal tip that selectively keys with a central opening of the anchor body. The distal tip can define longitudinal slits formed therealong that are configured to permit suture to pass through. The distal tip can create a friction fit with the central opening of the anchor body. The distal tip can include at least one of an increased outer diameter portion and an o-ring.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 1 a perspective view of a suture anchor constructed in accordance to one example of the present disclosure;

FIG. 2 is a cross-sectional view of the suture anchor taken along lines 2-2 of FIG. 1;

FIG. 3 is a side view of an exemplary flexible member securing assembly in accordance with various aspects of the present disclosure and shown in an alignment position cooperating with a suture and the suture anchor of FIG. 1;

FIG. 4 is a cross-sectional view of the flexible member securing assembly taken along lines 4-4 of FIG. 3;

FIG. 5 is a side view of the flexible member securing assembly of FIG. 3 and shown in an insertion position;

FIG. 6 is a side view of the flexible member securing assembly of FIG. 5 and shown in a driven position subsequent to driving the suture anchor into bone;

FIG. 9 is a cross-sectional view of a suture anchor constructed in accordance to additional features of the present disclosure;

FIGS. 10-11 depict an exemplary method of using a primary and secondary suture anchor according to the present disclosure;

FIG. 14 is a side view of an exemplary insertion tool constructed in accordance to one example of the present disclosure;

FIG. 15 is a side view of an inserter tip constructed in accordance to additional features;

FIG. 16 is a side view of another inserter tip constructed in accordance to further features of the present disclosure; and FIG. 17 is a side view of another inserter tip constructed in accordance to additional features of the present disclosure.

DETAILED DESCRIPTION

Figure 7:
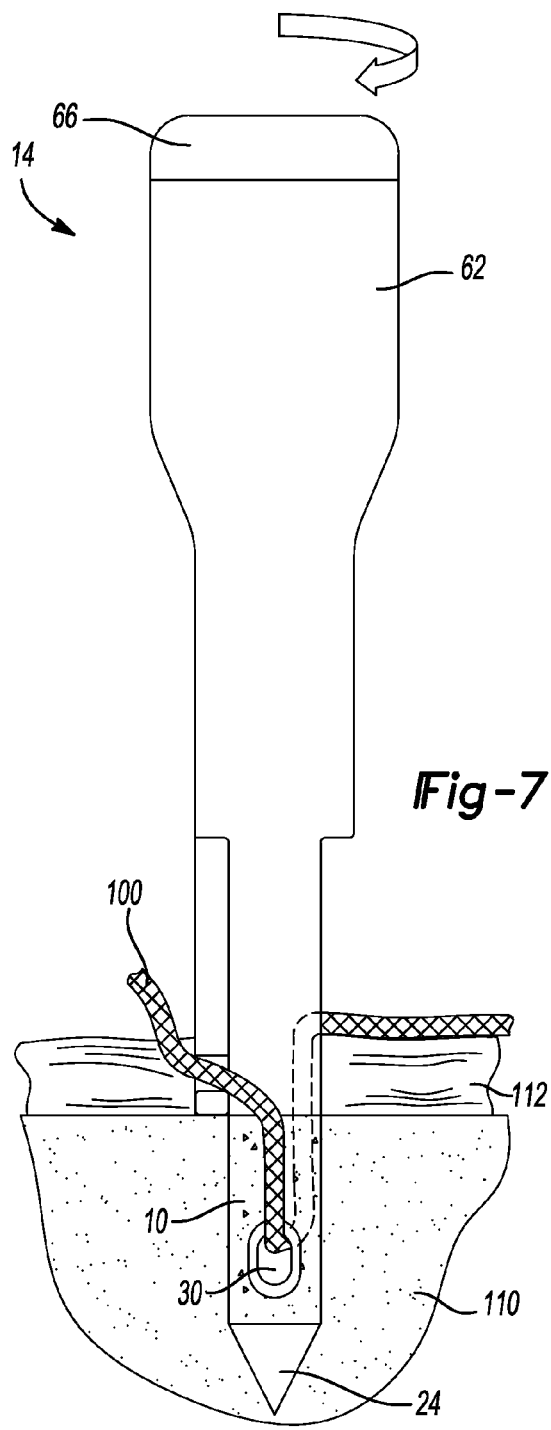
FIG. 7 is a side view of the flexible member securing assembly of FIG. 6 shown with a sleeve portion rotated to free an end of the suture anchor from a suture engaging portion on the sleeve portion.
Figure 8:
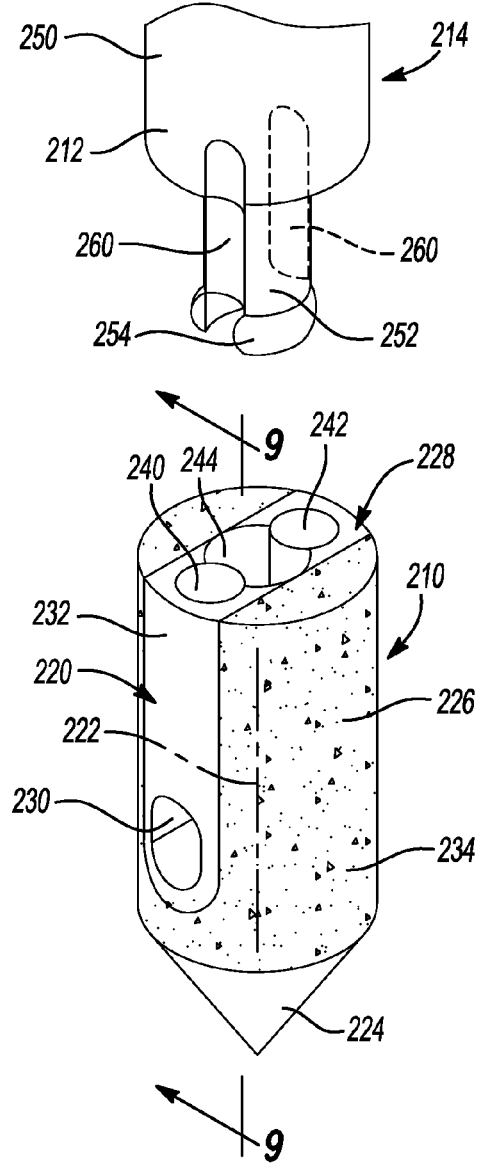
FIG. 8 is a partial exploded perspective view of a suture anchor and insertion tool constructed in accordance to additional features of the present disclosure.

The following description is merely exemplary in nature and is not intended to limit the present disclosure, its application, or uses. Although the following description is related generally to methods and apparatus for securing a flexible member to bone, it should be appreciated that the methods and apparatus discussed herein can be applicable to various bones and/or joints of the anatomy and can be utilized with various flexible members and rigid bodies or anchors.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide a flexible member securing assembly and a method for using the same to secure a flexible member to bone. In an exemplary aspect, the flexible member can be a suture and the rigid body can be an anchor. In an exemplary aspect, the flexible member securing assembly can include an impacting portion and a sleeve portion movably coupled to each other and provided preassembled in a kit. In another exemplary aspect, the kit can further include an anchor. The present teachings further disclose various alternate insertion tools that are selectively and removably coupled to the anchor.

With initial reference to FIGS. 1-7, a suture anchor constructed in accordance to one example of the present disclosure is shown and generally identified at reference numeral 10. The suture anchor 10 can be provided together such as in a kit with an inserter assembly 12 as a suture securing assembly 14. As will become appreciated from the following discussion, the inserter assembly 12 can cooperate with the suture anchor 10 and be used to drive the suture anchor 10 into bone. While the suture anchor 10 and inserter assembly 12 will be described herein as cooperating as a suture securing assembly 14, it will be appreciated that the suture anchor 10 and the inserter assembly 12 can be used separately. In this regard, the suture anchor 10 can be used with other inserter assemblies while the inserter assembly 12 can be used to drive other suture anchors into bone.

With particular reference to FIGS. 1 and 2, the suture anchor 10 will be further described. The suture anchor 10 generally comprises an anchor body 20 that extends along a longitudinal anchor body axis 22. The anchor body 20 can include a distal tip portion 24, a proximal body portion 26 and an impactor engaging surface or proximal stem portion 28. An eyelet 30 can be formed through the proximal body portion 26. In the example shown, the eyelet 30 has a substantially oval shape; however, other configurations are contemplated. As will become appreciated from the following discussion, the eyelet 30 can be used during knotless suture fixation.

The anchor body 20 can include a solid anchor portion 32 and a porous anchor portion 34. In the example shown, the porous anchor portion 34 can have a nesting porous portion 36, an intermediate porous portion 38 and a proximal porous portion 40. The nesting porous portion 36 can be formed generally intermediate the distal tip portion 24 and the eyelet 30. The intermediate porous portion 38 can be formed generally around the eyelet 30. The proximal porous portion 40 can be formed generally proximal of the eyelet 30. In the example shown, the eyelet 30 is formed exclusively by the solid anchor portion 32. In one example, the solid anchor portion 32 can have a wall thickness 42 (FIG. 2) at the eyelet 30 of at least 0.5 mm and preferably between 0.5 mm and 0.75 mm. Other configurations are contemplated. The solid anchor portion 32 that forms the eyelet 30 can provide a rigid structure for suture to engage. As will be described herein, the proximal stem portion 28 can be used to interface with the inserter assembly 12 and can be removed from the remainder of the suture anchor 10 subsequent to insertion of the suture anchor 10 into bone.

The solid portion 32 of the suture anchor 10 can be formed of any appropriate biocompatible material including polymers, co-polymers, such as polyetheretherketone (PEEK), metals, such as titanium, and various alloys, formed from titanium, cobalt, chromium, etc. The porous portion 34 can include stainless steel, titanium, titanium alloys, cobalt-chromium alloys, PEEK, Polyetherketoneketone (PEKK) and other materials that are suited for use in a biocompatible environment including Regenerex™, a porous titanium construct manufactured from Ti-6Al-4V alloy and commercially available from Biomet, Inc., of Warsaw, Ind. The porous portion 34 can be adapted to receive bone ingrowth through interstitial space at ports defined therein. Furthermore, the porous portion 34 includes a rough surface that can facilitate initial fixation into bone. The porous portion 34 can create enhanced fixation to the bone in a shorter time frame compared to suture anchors formed exclusively of solid material.

With particular attention now to FIGS. 3-7, the inserter assembly 12 will be further described. The inserter assembly 12 can generally include an impacting portion 60 and a sleeve portion 62. The impacting portion 60 can extend along a longitudinal impacting portion axis 64 and have a strike plate 66 and a shaft portion 68. The shaft portion 68 can define a suture engaging surface or blind bore 70 having a terminal engaging surface 72. A first threaded portion 76 can be formed around the shaft portion 68.

The sleeve portion 62 can generally extend between a handle portion 80 and a distal suture engaging end 82. The handle portion 80 defines a central passage 84. The sleeve portion 62 can include a second threaded portion 88 that is configured to threadably mate with the first threaded portion 76 of the impacting portion 60. The distal suture engaging end 82 includes a suture engaging member 90. In the example shown, the suture engaging member 90 is in the form of a hook although other geometrical configurations suitable for grasping a suture are contemplated. The suture engaging member 90 defines an opening 92 (FIG. 5) and a suture nesting slot 94.

As will be described herein, the inserter assembly 12 is movable between an alignment position (FIGS. 3 and 4), an insertion position (FIG. 5) and a driven position (FIG. 6). In general, the inserter assembly 12 can be used to position a suture 100 in a desired location relative to the eyelet 30 to account for a length 102 (FIG. 5) of the suture 100 that will be driven into bone 110. Explained further, the suture engaging member 90 of the sleeve portion 62 can engage the suture 100 at an offset position (FIG. 5) relative to the eyelet 30 to define the length 102 of the suture 100 that will be pulled into bone 110. Because the length 102 of the suture 100 has been accounted for prior to driving the suture anchor 10 into the bone 110 (FIG. 5), the suture 102 will not be over-tightened on tissue 112 as a result of advancing the suture anchor 10 into the bone 110 (FIG. 6).

An exemplary method of securing the soft tissue 112 to the bone 110 using the suture securing assembly 14 will now be described. Initially, the suture anchor 10 can be positioned with respect to the inserter assembly 12. In one example, the proximal stem portion 28 of the suture anchor 10 can be inserted into the blind bore 70 of the shaft portion 68 of the inserter assembly 12. The proximal stem portion 28 can be further advanced until a terminal proximal end 114 of the proximal stem portion 28 engages or bottoms out onto the engaging surface 72 (FIG. 3). Additionally or alternatively, the proximal stem portion 28 can be advanced into the blind bore 70 until a distal engaging end 116 (FIG. 3) on the shaft portion 68 engages a proximal engaging surface 118 on the suture anchor 10. In one configuration, the long axis 22 of the suture anchor 10 is coaxial with the impacting portion axis 64.

The suture 100 can then be threaded through the eyelet 30. It will be appreciated that the suture 100 may have been threaded through the eyelet 30 prior to advancing the proximal stem portion 28 into the blind bore 70. Next, the suture engaging member 90 is hooked around the suture 100 (FIGS. 3 and 4). In some examples, the suture 100 may be threaded through the eyelet 30 and the suture nesting slot 94 in one motion. At this point it is important to recognize that the strike plate 66 is offset from the sleeve portion 62 a first distance 120 (FIG. 4).

The distal tip 24 can be initially advanced slightly into the bone 110 as shown in FIG. 5. With the suture engaging member 90 hooked around the suture 100, the sleeve portion 62 is rotated around the impacting portion axis 64 causing the sleeve portion 62 to move upwardly (as viewed from FIG. 4) relative to the impacting portion 60. Specifically, the first and second threaded portions 76 and 88 cooperate to permit the sleeve portion 62 to move from the alignment position (FIG. 4) to the insertion position (FIG. 5). Notably, as the first distance 120 closes, the suture engaging member 90 moves a second distance 122 upward and away from the distal tip 24. As the sleeve portion 62 translates upward, the suture engaging member 90 slidably negotiates along the suture 100. In the example provided, the first distance 120 is substantially equivalent to the second distance 122. While the exemplary mechanical configuration described herein includes cooperating threaded portions 76 and 88, other configurations are contemplated for providing relative movement between the sleeve portion 62 and the impacting portion 60. Moreover, while the above description identifies the sleeve portion 62 as being rotated, it will be appreciated that one or both of the sleeve portion 62 and the impacting portion 60 can be rotated to cause relative movement therebetween.

According to one exemplary method, once the inserter assembly 12 is in the insertion position (FIG. 5) and the length 102 of suture 100 is accounted for, the suture 100 can be tightened relative to the tissue 112. As explained above, because the length 102 of the suture 100 is created, driving the suture anchor 10 into the bone 110 will not further tighten the suture 100 on the tissue 112. The inserter assembly 12 can then be used to drive the suture anchor 10 into the bone 110 (FIG. 6). In one example, the strike plate 66 is impacted such as with an impacting tool (not shown) causing an impacting force to be communicated from the engaging surface 72 of the shaft portion 68 to the suture anchor 10 such as on the terminal proximal end 114 of the proximal stem portion 28. The strike plate 66 may be impacted one or many times until the inserter assembly 12 reaches the driven position (FIG. 6) and the suture anchor 10 is driven into the bone 110. After the suture anchor 10 has been driven into the bone 110, the sleeve portion 62 can be rotated until the suture engaging member 90 releases the suture 100 as depicted in FIG. 7. The inserter assembly 12 can then be removed from the suture anchor 10. The proximal stem portion 28 can then be cut off or otherwise removed from a remainder of the suture anchor 10.

With reference now to FIGS. 8-11, a suture anchor 210 constructed in accordance to additional features of the present disclosure will be described. The suture anchor 210 can be provided together such as in a kit with an insertion tool 212 as a suture securing assembly 214. Alternatively, the suture anchor 210 and the insertion tool 212 may be provided separately and do not require each other for operation.

The suture anchor 210 generally comprises an anchor body 220 that extends along a longitudinal anchor body axis 222. The anchor body 220 can include a distal tip portion 224, and a proximal body portion 226. The proximal body portion 226 can have a proximal terminal end surface 228. An eyelet 230 can be formed through the proximal body portion 226. In the example shown, the eyelet 230 has a substantially oval shape however other configurations are contemplated.

The anchor body 220 can include a solid anchor portion 232 and a porous anchor portion 234. The solid and porous anchor portions 232 and 234 can be formed from the materials described above with respect to the suture anchor 10. The anchor body 220 can further define a first longitudinal opening 240, a second longitudinal opening 242 and a central opening 244. The first and second longitudinal openings 240 and 242 connect with the eyelet 230 (FIG. 9). In one example, the eyelet 230, the first longitudinal opening 240, the second longitudinal opening 242 and the central opening 244 are all formed in the solid anchor portion 232 for increased strength.

The insertion tool 212 can include an insertion tool body 250 and an inserter tip 252. The inserter tip 252 can define an increased diameter portion 254 configured to provide a friction fit with the central opening 244. The insertion tool 212 can further include longitudinal slits 260 that run along the inserter tip 252 and a portion of the insertion tool body 250. As will be described, the longitudinal slits 260 provide a pathway to accommodate suture extending out of either the first or second longitudinal openings 240 and 242 (FIG. 10).

With particular attention now to FIGS. 9 and 10, an exemplary method of using the suture anchor 210 will be described. The suture anchor 210 is particularly versatile as it can be used for either primary fixation (solid suture 300, FIG. 9) or secondary fixation (phantom suture 300, FIG. 9). In this regard, the eyelet 230 can be used to receive suture 300 when used for secondary fixation. Those skilled in the art will recognize that secondary fixation is a knotless fixation where a portion of the suture 300 may be pinched between an inner diameter of the bone hole and an outer circumference of the suture anchor 310. When the suture anchor 210 is used for secondary fixation, one of the first and second longitudinal openings 240 and 242 can be used to thread the suture 300 and the suture 300 can extend out of the eyelet 230 (phantom view suture 300, FIG. 9).

As viewed in FIG. 9, in one method, the suture (represented as solid line 300) can be threaded down one of the first and second longitudinal openings 240 and 242, to the eyelet 230 and up the other of the first and second longitudinal openings 240 and 242. In another method, the suture (represented as phantom line 300) can be threaded down one of the first and second longitudinal openings 240 and 242 and out the eyelet 230. In either scenario, one end of the suture 300 that extends out from the proximal terminal end surface 228 will be free. In this regard, the suture 300 is free to slidably negotiate out of the first longitudinal opening 240 during driving of the suture anchor 210 into the bone. Further, a desired amount of tension can be applied to the suture 300 relative to the tissue 312. Over-tightening of the suture 300 around the tissue 312 as a result of driving the suture anchor 210 into the bone can be avoided.

Figure 11:
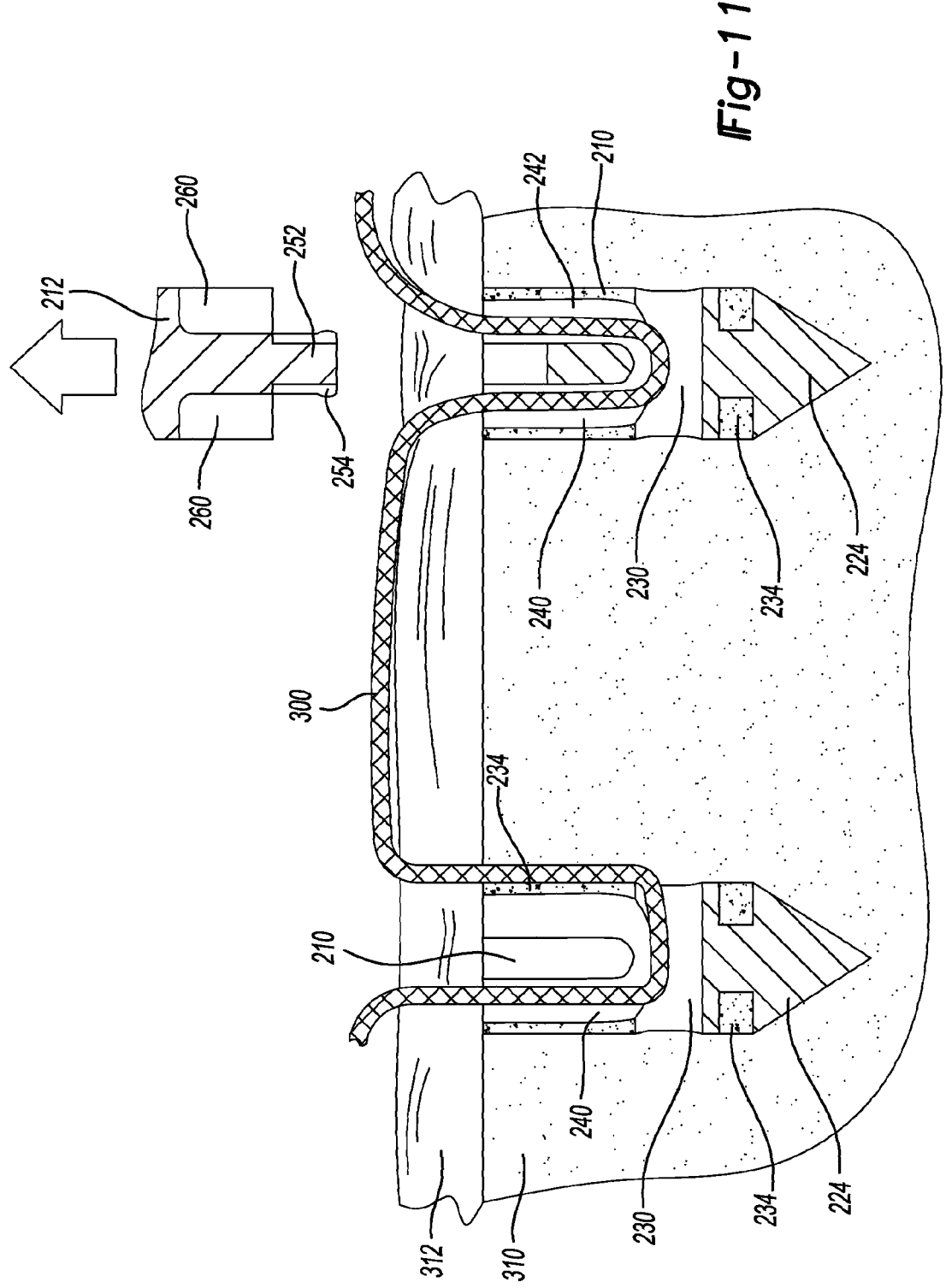

In FIG. 10, the leftmost anchor 210 is shown with the suture 300 threaded for use in primary fixation. The rightmost anchor 210 is shown with the suture 300 in solid line threaded for primary fixation or alternately for secondary fixation (phantom line). In FIG. 11, the rightmost anchor 210 is shown with the suture 300 threaded through the first and second longitudinal openings 240 and 242 for use in primary fixation. The leftmost anchor 210 is shown with the suture 300 threaded through the first longitudinal opening 240 and between an outer diameter of the suture and an inner diameter of the bone 310 for use in secondary fixation.

Figure 12:
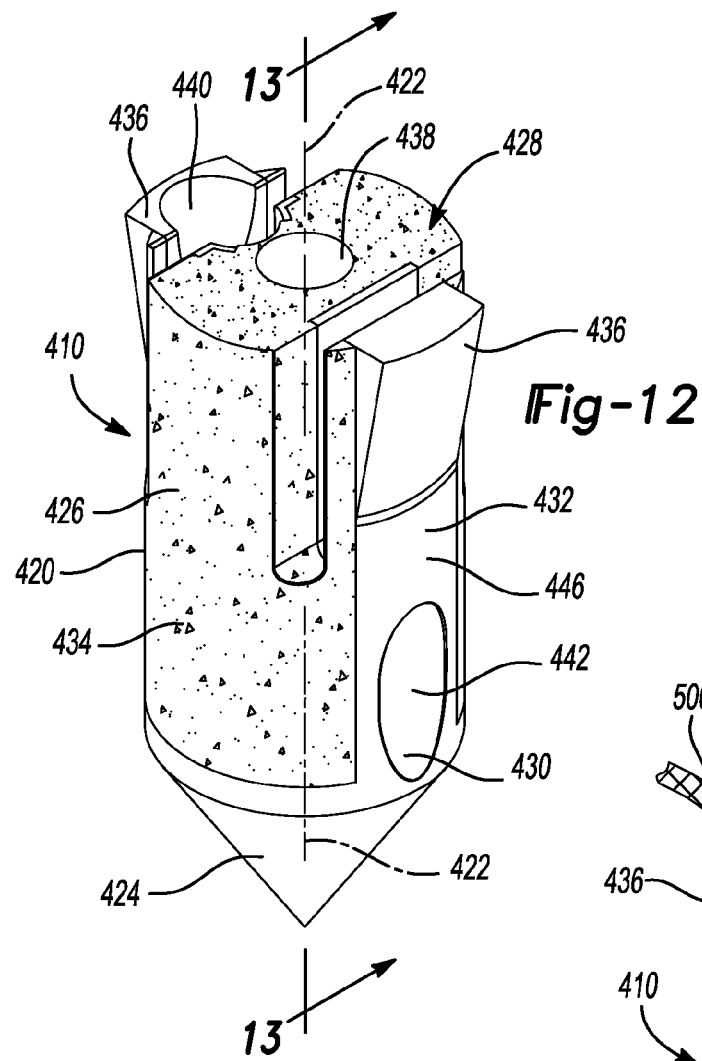
FIG. 12 is a perspective view of another suture anchor constructed in accordance to additional features of the present disclosure.
Figure 13:
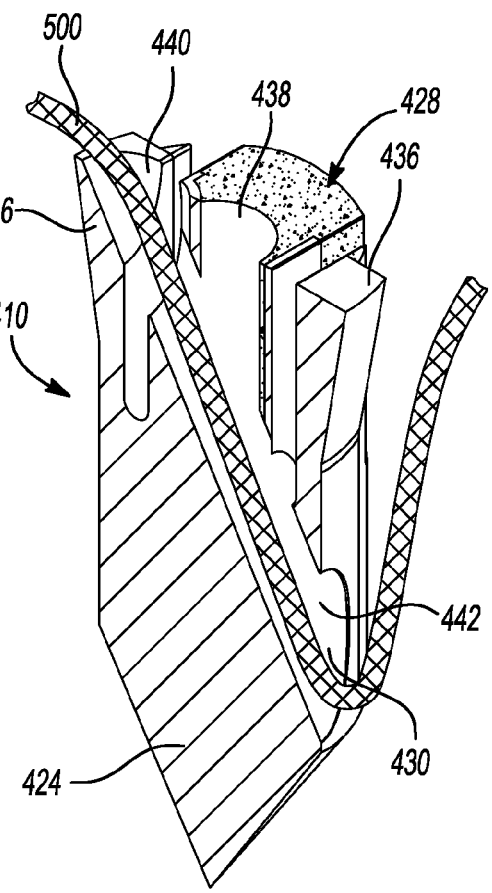
FIG. 13 is a cross-sectional view taken along lines 13-13 of the suture anchor of FIG. 12.

With reference now to FIGS. 12, 13 and 16, a suture anchor 410 constructed in accordance to additional features of the present disclosure will be described. The suture anchor 410 can be provided together such as in a kit with an insertion tool 412 (FIG. 16) as a suture securing assembly. Alternatively the suture anchor 410 and the insertion tool 412 may be provided separately and do not require each other for operation.

The suture anchor 410 generally comprises an anchor body 420 that extends along a longitudinal anchor body axis 422. The anchor body 420 can include a distal tip portion 424, and a proximal body portion 426. The proximal body portion 426 can have a proximal terminal end surface 428. An eyelet 430 can be formed through the proximal body portion 426. In the example shown, the eyelet 430 has a substantially oval shape however other configurations are contemplated.

The anchor body 420 can include a solid anchor portion 432 and a porous anchor portion 434. The solid and porous anchor portions 432 and 434 can be formed from the materials described above with respect to the suture anchor 10. The anchor body 420 can further include a pair of flexible wing portions 436 extending outwardly from the anchor body 420. The flexible wing portions 436 can be configured to contract during insertion and provide a radially outwardly biasing force onto surrounding bone once inserted to inhibit withdrawal of the suture anchor 410 from the bone. A central opening 438 can be formed in the proximal terminal end surface 428.

The eyelet 430 can be formed through the anchor body 420 from a first opening 440 at the proximal end surface 428 to a second opening 442 through an outer cylindrical wall of the anchor body 420. In one example, the first opening 440 can extend through one of the flexible wing portions 436. In one example, the eyelet 430 and the flexible wing portions 436 are all formed in the solid anchor portion 432.

One method of using the suture anchor 410 will now be described. A suture 500 can be threaded into the first opening 440 and out of the second opening 442. Because the first opening 440 extends out through the proximal terminal end surface 428, the suture 500 will not be pinched between the anchor body 420 and the inner diameter of the bone hole during insertion of the suture anchor 410. In this regard, an end of the suture 500 extending out of the first opening 440 is free to slide during insertion of the suture anchor 410 into the bone hole. Similar to the function of the longitudinal openings 240 and 242 of the suture anchor 310, a free end of the suture 500 can preclude over-tightening of the suture anchor 410 during insertion into bone. As a result, the suture anchor 410 can be particularly useful for secondary fixation.

The insertion tool 412 can include an inserter tip 470 configured to be received into the central opening 438 of the suture anchor 410. A raised diameter portion 472 can be in the form of an elastomeric member or o-ring. The raised diameter portion 472 can be configured to attain a friction or interference fit with the central opening 438. Another insertion tool 480 shown in FIG. 14 can include an inserter tip 482 and a handle 484. The handle 484 can be connected to the inserter tip 482 by a shaft 486. Another insertion tool 512 shown in FIG. 15 includes an insertion tip 514 having a raised diameter portion 516. The raised diameter portion 516 can be in the form of an elastomeric member or o-ring. The raised diameter portion 516 can be configured to attain a friction or interference fit with the central opening 244 or 438. Another insertion tool 532 shown in FIG. 17 includes an insertion tip 534 having a raised diameter portion 536. The raised diameter portion 516 can be in the form of an elastomeric member or o-ring. The insertion tip 534 can include a pointed distal end 540 configured to extend through an anchor.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A suture securing assembly for use in securing a suture relative to bone, the assembly comprising:
   an impacting portion extending along a first longitudinal axis, the impacting portion having a strike plate and a shaft portion that defines a suture anchor engaging surface;
   a sleeve portion movably coupled to the impacting portion, the sleeve portion having a central passage that receives the impacting portion therethrough, the sleeve portion having a suture engaging member formed at a distal end; and
   an anchor having an anchor body and a proximal stem, the anchor body includes a solid anchor portion defining a distal tip portion, a porous anchor portion defining a longitudinal opening and an impactor engaging surface, and an eyelet defined by and extending through the solid anchor portion, wherein the proximal stem portion is configured to be slidably received by the suture anchor engaging surface and extends from the longitudinal opening;
   wherein the sleeve portion is configured to translate relative to the impacting portion along the first longitudinal axis from an alignment position where the suture engaging member is aligned with the eyelet to an insertion position where the suture engaging member moves the suture to a location offset a distance from the eyelet in a direction away from the distal tip.

2. The suture securing assembly of claim 1 wherein the sleeve portion is coupled to the impacting portion and wherein rotation of one of the sleeve portion and the impacting portion about the first longitudinal axis causes the one of the sleeve portion and the impacting portion to translate relative to the other of the sleeve portion and the impacting portion.

3. The suture securing assembly of claim 1 wherein the suture engaging member comprises a hook.

4. The suture securing assembly of claim 1 wherein the strike plate is configured to engage the sleeve portion at the insertion position thereby inhibiting further relative translation of the sleeve portion and the impacting portion.

5. The suture securing assembly of claim 1, wherein the anchor body extends along a longitudinal axis, and wherein the eyelet extends from a first side surface to a second side surface.

6. The suture securing assembly of claim 1, wherein the central passage of the sleeve portion includes a first threaded portion.

7. The suture securing assembly of claim 6, wherein the shaft portion a second threaded portion that is configured to engage with the first threaded portion to couple the sleeve portion to the impacting portion.

8. The suture securing assembly of claim 1, wherein the porous anchor portion includes a nesting porous portion that is located between the distal tip and the eyelet.

9. A suture securing assembly for use in securing a suture relative to bone, the assembly comprising:

an impacting portion extending along a first longitudinal axis, the impacting portion having a strike plate and a shaft portion that defines a suture anchor engaging surface;

a sleeve portion movably coupled to the impacting portion, the sleeve portion having a central passage that receives the impacting portion therethrough, the sleeve portion having a suture engaging member formed at a distal end; and an anchor having an anchor body that includes a solid anchor portion and a porous anchor portion surrounding a portion of the solid anchor portion, wherein the solid anchor portion includes a distal tip, an eyelet, and a stem portion, and wherein the porous anchor portion includes a nesting porous portion and a proximal porous portion, the nesting porous portion located between the distal tip and the eyelet and the proximal porous portion defining a longitudinal opening extending along the proximal porous portion, wherein the stem portion extends from the longitudinal opening.

10. The suture securing assembly of claim 9, wherein the sleeve portion is configured to translate relative to the impacting portion along the first longitudinal axis from an alignment position where the suture engaging member is aligned with the eyelet to an insertion position where the suture engaging member moves the suture to a location offset a distance from the eyelet in a direction away from the distal tip.

\* \* \* \* \*